United States Patent [19]

Rühl et al.

[11] Patent Number: 5,654,478

[45] Date of Patent: Aug. 5, 1997

[54] PREPARATION OF N-ALKENYLCARBOXAMIDES

[75] Inventors: Thomas Rühl, Frankenthal; Jochem Henkelmann, Mannheim; Marc Heider, Neustadt; Bernd Fiechter, Böhl-Iggelheim, all of Germany

[73] Assignee: BASF Aktiengesellschaft, Ludwigshafen, Germany

[21] Appl. No.: 513,739

[22] Filed: Aug. 10, 1995

[30] Foreign Application Priority Data

Aug. 19, 1994 [DE] Germany ............ 44 28 901.4

[51] Int. Cl.$^6$ .................. C07C 231/08

[52] U.S. Cl. .......... 564/135; 564/133; 564/134; 564/137; 564/139; 564/183; 564/189; 564/190; 564/215

[58] Field of Search ............ 564/134, 135, 564/137, 139, 183, 189, 190, 215, 133

[56] References Cited

U.S. PATENT DOCUMENTS

| | | | |
|---|---|---|---|
| 4,490,557 | 12/1984 | Dawson et al. | 564/159 |
| 4,567,300 | 1/1986 | Murao et al. | 564/215 |
| 4,670,531 | 6/1987 | Eckberg | 528/15 |
| 4,670,591 | 6/1987 | Oftring et al. | 564/224 |
| 4,968,841 | 11/1990 | Listemann et al. | 564/159 |
| 5,023,375 | 6/1991 | Listemann | 564/159 |

FOREIGN PATENT DOCUMENTS

| | | |
|---|---|---|
| 184 074 | 6/1986 | European Pat. Off. . |
| 3622013 | 1/1986 | Germany . |
| 3443463 | 5/1986 | Germany . |

OTHER PUBLICATIONS

*Das Papier*, 46/10A (1992), pp. V38–V45.
*App. Cataly.*, 78 (1991) p. 65.
Allred et. al., J. Org. Chem., vol. 30, pp. 2376–2381 1965.

*Primary Examiner*—Shailendra Kumar
*Attorney, Agent, or Firm*—Keil & Weinkauf

[57] ABSTRACT

N-Alkenylcarboxamides of the formula I

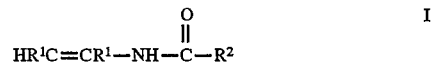

where at least one of the radicals $R^1$ is hydrogen, the second radical $R^1$ is hydrogen or $C_1$–$C_4$-alkyl and $R^2$ is hydrogen or an aliphatic, cycloaliphatic or aromatic radical, are prepared by reacting an alkenyl carboxylate of the formula II

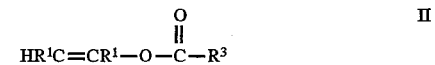

where $R^1$ has the abovementioned meanings and $R^3$ is hydrogen or an aliphatic, cycloaliphatic or aromatic radical, and a carboxamide of the general formula III

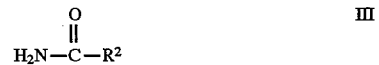

where $R^2$ has the abovementioned meanings, in the presence of a base.

8 Claims, No Drawings

PREPARATION OF N-ALKENYLCARBOXAMIDES

BACKGROUND OF THE INVENTION

1. Field of the Invention

The present invention relates to a novel process for the preparation of N-alkenylcarboxamides of the formula I $$HR^1C=CR^1-NH-\overset{O}{\underset{\|}{C}}-R^2 \qquad I$$

where at least one of the radicals $R^1$ is hydrogen, the second radical $R^1$ is hydrogen or $C_1$–$C_4$-alkyl and $R^2$ is hydrogen or an aliphatic, cycloaliphatic or aromatic radical.

The products of the formula I are desirable intermediates. N-Alkenylcarboxamides can be polymerized in a known manner and then converted by hydrolysis into the corresponding polyvinylamines. These polymers, in particular polyvinylformamine, are used, for example, for the preparation of dyes, pharmaceutical products, flocculants and viscosity standardizing agents in the paper industry (Linhard et al., Das Papier 46/10A (1992), p. V 38–45).

2. Description of the Related Art

N-Vinylformamide can be prepared by pyrolytic cleavage of ethylideneformamide at from about 300° to 400° C. Ethylideneformamide can be prepared, for example under mercury catalysis in acidic solution, from formamide and vinyl acetate (DE-A 40 36 097) or from formamide and acetaldehyde in the presence of acidic catalysts (U.S. Pat. No. 4,490,557).

Other methods of preparation are via intermediates such as N-acetylethylformamide (G. Parris, App. Cataly., 78 (1991) 65), N-alkoxyethylformamide (DE-A 3 622 013, DE-A 3 520 829 and U.S. Pat. No. 4,670,531), N-hydroxyethylformamide (U.S. Pat. No. 4,567,300) and N-cyanoethylformamide (DE-A 3 443 463). These compounds eliminate acetic acid, alcohols, water and hydrogen cyanide, respectively at relatively high temperatures of approximately 300° to 400° C.

The stated preparation processes are two-stage and require a thermal elimination step. They are thus technically relatively complicated and, owing to losses of end product at the required high reaction temperatures, give only unsatisfactory total yields. It is an object of the present invention to provide a process which avoids the stated disadvantages of known processes.

SUMMARY OF THE INVENTION

We have found that this object is achieved by a process for the preparation of N-alkenylcarboxamides of the formula I, which comprises reacting an alkenyl carboxylate of the general formula II $$HR^1C=CR^1-O-\overset{O}{\underset{\|}{C}}-R^3 \qquad II$$

where $R^1$ has the abovementioned meanings and $R^3$ is hydrogen or an aliphatic, cycloaliphatic or aromatic radical, and a carboxamide of the formula III $$H_2N-\overset{O}{\underset{\|}{C}}-R^2 \qquad III$$

where $R^3$ has the abovementioned meanings, in the presence of a base.

The equation below illustrates the claimed process, using as an example the preparation of N-vinylformamide from vinyl formate and formamide in the presence of triethylamine (Et=ethyl):

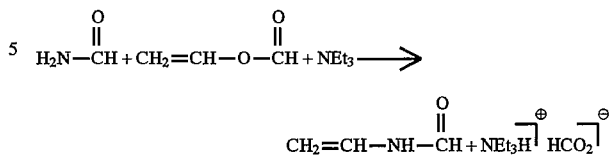

In the novel process, a vinyl group is formally transferred from a vinyl carboxylate of the formula II to a carboxamide of the formula III.

DESCRIPTION OF PREFERRED EMBODIMENTS

The alkenyl group of the esters of the formula II may carry a $C_1$–$C_4$-alkyl radical, such as methyl, ethyl, n-propyl, isopropyl or n-butyl, the preferred compounds are those in which $R^1$ is hydrogen. $R^3$ in the esters of the formula II is an aliphatic radical, such as alkyl or alkenyl, each of which is preferably of 1 to 40 carbon atoms and may be straight-chain or branched. $C_1$–$C_{20}$-Alkyl groups, such as methyl, ethyl n-propyl, n-butyl, tert-butyl and stearyl, are preferred. $R^3$ may furthermore be a cycloaliphatic radical, preferably of 4 to 7 carbon atoms, eg. cyclopentyl or cyclohexyl. Aromatic radicals, such as phenyl and naphthyl, are also suitable and they may carry substituents which are inert under the reaction conditions, such as halogen and alkoxy. However, $R^3$ is particularly preferably hydrogen. Examples of starting compounds of the formula II are vinyl formate, vinyl acetate and vinyl stearate. The compounds of the formula II are commercially available or can be prepared by known methods, for example by addition reaction of carboxylic acids with acetylene.

The statements made above for the radical $R^3$ are applicable to the radical $R^2$ of the amides of the formula III. Examples of starting compounds are formamide, acetamide and acrylamide. These compounds, too, are commercially available or obtainable by known methods, for example by reacting a carboxylic acid and ammonia with elimination of water. The preferred product is N-vinylformamide.

The starting compounds are reacted in the presence of a base, preferably a Brönsted base. Both inorganic bases and organic bases are suitable in this case. These are specifically carbonates and bicarbonates of the alkali and alkaline earth metals, such as sodium carbonate, potassium carbonate and sodium bicarbonate, quaternary ammonium carbonates, such as tetramethylammonium carbonate, amides, such as alkali metal amides, for example sodium amide and potassium amide, hydroxides, such as alkali metal hydroxides, for example lithium hydroxide; sodium hydroxide and potassium hydroxide, alkali metal carboxylates, such as sodium acetate, alcoholates, such as alkali metal alcoholates, for example sodium methylate, sodium ethylate, potassium methylate and potassium tert-butylate. Potassium hydroxide may also be used together with crown ethers, such as 18-crown-6.

Other suitable bases are amines, such as ammonia and primary, secondary and tertiary amines, among which the tertiary amines are preferred. The amines may carry aliphatic, cycloaliphatic or aromatic radicals and may be, for example, trialkylamines, such as trioctylamine, ethyldiisopropylamine, diethylisopropylamine, dimethylcyclohexylamine and triethylamine, as well as cyclic amines, such as 2,2,6,6-tetramethylpiperidine, 1,4-diazabicyclo [2.2.2]octane, 1,8-diazabicyclo[5.4.0]undec-7-ene and 1,5-diazabicyclo[4.3.0]non-5 ene, amines carrying aliphatic and aromatic radicals, such as 1,8-bis(dimethylamino) naphthalene and 4-dimethylaminopyridine, and heterocyclic amines, such as N-alkylimidazoles and N-arylimidazoles, eg. N-methylimidazole and N-butylimidazole. Amides, such as dialkylcarboxamides, eg. dibutylformamide, are also suitable.

The novel process can also be carried out in the presence of basic ion exchangers, which as a rule consist of sulfonated styrene/divinylbenzene copolymers, such as Amberlite®, Lewatit® and Puralit®, and in the presence of basic zeolites, such as hydrotalcite.

From 0.1 to 10, preferably from 0.5 to 2, equivalents of the ester of the formula II may be used per equivalent of the amide of the formula III.

The amount of base may be from 0.1 to 3 equivalents, preferably from 0.2 to 1 equivalent, per equivalent of amide of the formula III.

Although the reaction is preferably carried out without solvent, a solvent may however be added, for example an aprotic solvent, such as an ether, eg. tetrahydrofuran, an aromatic hydrocarbon, such as toluene or xylene, a ketone, such as acetone, or acetonitrile, hexamethylphosphorotriamide, sulfolane or dimethyl sulfoxide. The amount is in general from 10 to 30% by weight, based on the total batch.

The reaction temperature is as a rule from 10° to 100° C., preferably from 20° to 60° C. Atmospheric pressure is preferably used, but it is also possible to employ a reaction pressure of from 0.01 to 10 bar.

The reaction may be carried out continuously or batchwise. Thus, the starting compounds and the base may be introduced into a stirred kettle and reacted therein. It is also possible to react the starting compounds and the base in a tube reactor by the trickle-bed or liquid phase method.

As a rule, the reaction is complete after 5 minutes to 8 hours.

The reaction mixture thus obtained can be worked up in a manner known per se. In general, the product is separated off by distillation. Alkalis, such as sodium hydroxide solution, may be added to the bottom product of the distillation in order to liberate the organic bases from the salts obtained in the reaction. The liberated bases can then be isolated by extraction or distillation. If readily volatile salt-like compounds, such as formates of tertiary ammonium compounds, are formed in the reaction according to the invention, they can also be worked up by distillation and converted into the corresponding amines. The bases separated off in each case can be recycled to the reaction.

The novel process permits the one-stage preparation of N-alkenylamides from readily available intermediates. The reaction is technically simple and takes place under mild reaction temperatures. It also gives the products in high yield.

EXAMPLES

General Reaction Procedure 0.3 mol of an ester of the formula II, 0.3 mol of an amide of the formula III and 0.15 mol of a base were reacted at 60° C. and at atmospheric pressure for 5 hours.

Conversion and selectivity were determined by gas chromatography.

The table below gives details of the reactions:

| Ex. | Amide | Ester | Base | Conversion [%] | Selectivity [%] |
|---|---|---|---|---|---|
| 1 | Formamide | Vinyl acetate | DMAP | 65 | 92 |
| 2 | Formamide | Vinyl propionate | DMAP | 62 | 95 |
| 3 | Acetamide | Vinyl formate | DMAP | 57 | 87 |
| 4 | Formamide | Vinyl formate | Triethylamine | 95 | 92 |
| 5 | Formamide | Vinyl formate | Dimethylcyclohexylamine | 92 | 87 |
| 6 | Formamide | Vinyl formate | Trioctylamine | 20 | 70 |
| 7 | Formamide | Vinyl formate | DABCO | 85 | 89 |
| 8 | Formamide | Vinyl formate | DBU | 73 | 86 |
| 9 | Formamide | Vinyl formate | DMAP | 97 | 94 |
| 10 | Formamide | Vinyl formate | Methylimidazole | 89 | 92 |
| 11 | Formamide | Vinyl formate | Dibutylformamide | 5 | 92 |
| 12 | Formamide | Vinyl formate | Ion exchanger Amberlite ® IRA 420 | 91 | 87 |
| 13 | Formamide | Vinyl formate | Hydrotalcite | 80 | 78 |
| 14 | Formamide | Vinyl formate | $Na_2CO_3$ | 97 | 82 |
| 15 | Formamide | Vinyl formate | $NaHCO_3$ | 92 | 89 |
| 16 | Formamide | Vinyl formate | $NaNH_2$ | 97 | 65 |
| 17 | Formamide | Vinyl formate | $NaOCH_3$ | 98 | 73 |
| 18 | Formamide | Vinyl formate | KOH | 82 | 58 |
| 19 | Formamide | Vinyl formate | KOH/18-K-6 | 83 | 63 |

DMAP = 4-Dimethylaminopyridine
DABCO = 1,4-Diazabicyclo [2.2.2]octane
DBU = 1,8-Diazabicyclo[5.4.0]undec-7-ene
18-K-6 = 18-crown-6

We claim:
1. A process for the preparation of an N-alkenylcarboxamide of the formula I

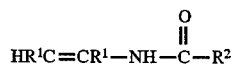

$$HR^1C=CR^1-NH-\underset{\underset{O}{\|}}{C}-R^2 \qquad I$$

where at least one of the radicals $R^1$ is hydrogen, the second radical $R^1$ is hydrogen or $C_1$–$C_4$-alkyl and $R^2$ is hydrogen or an aliphatic, cycloaliphatic or aromatic radical, which comprises reacting an alkenyl carboxylate of the formula II

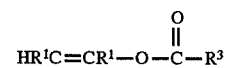

$$HR^1C=CR^1-O-\underset{\underset{O}{\|}}{C}-R^3 \qquad II$$

where $R^1$ has the abovementioned meanings and $R^3$ is hydrogen or an aliphatic, cycloaliphatic or aromatic radical, and a carboxamide of the formula III

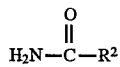

$$H_2N-\underset{\underset{O}{\|}}{C}-R^2 \qquad III$$

where $R^2$ has the abovementioned meanings, in the presence of a base.

2. The process of claim 1, wherein the radicals $R^1$ are hydrogen.

3. The process of claim 1, wherein $R^2$ is hydrogen or $C_1$–$C_{20}$-alkyl.

4. The process of claim 1, wherein N-vinylformamide is prepared.

5. The process of claim 1, wherein the reaction is carried out without solvent.

6. The process of claim 1, wherein the base used is a tertiary amine.

7. The process of claim 1, wherein from 0.2 to 1 equivalent of base is used per equivalent of amide of the formula III.

8. The process of claim 1, wherein the reaction is carried out at from 20° to 60° C.

* * * * *